United States Patent [19]

Mackal

[11] Patent Number: 5,238,218
[45] Date of Patent: Aug. 24, 1993

[54] TUBE CLAMP

[76] Inventor: Glenn H. Mackal, 2586 25th Ave. No., St. Petersburg, Fla. 33713

[21] Appl. No.: 897,176

[22] Filed: Jul. 15, 1992

[51] Int. Cl.$^5$ .............................................. F16K 7/04
[52] U.S. Cl. ...................................... 251/10; 604/34; 604/250
[58] Field of Search ...................... 251/10; 604/34, 250

[56] References Cited

U.S. PATENT DOCUMENTS

| | | | |
|---|---|---|---|
| 4,453,295 | 6/1984 | Laszczower | 251/10 |
| 4,588,160 | 5/1986 | Flynn et al. | 251/10 |
| 4,589,626 | 5/1986 | Kurtz et al. | 251/10 |
| 4,643,389 | 2/1987 | Elson et al. | 251/10 |

Primary Examiner—Gerald A. Michalsky
Attorney, Agent, or Firm—Joseph C. Mason, Jr.; Ronald E. Smith

[57] ABSTRACT

A tongue and groove construction maintains the catch and latch part of a tube clamp in full registration with one another across its entire range of positions from fully open to fully closed. A groove bisects the teeth of the latch member and a complementally formed tongue bisects the catch member of the clamp. Thus, when the tongue is slidably received within the groove, the parts of the catch member that flank the tongue releasably engage the parts of the latch member that flank the groove. This maintains the tube pinching elements in full alignment with one another so that when the pinching elements are fully displaced toward one another, no liquid fluid may flow through a cannula disposed therebetween. The teeth are not provided in a second embodiment, but the tongue and groove arrangement is employed in that embodiment. The tongue engages the underside of a lip, and the clamp is either fully open or fully closed.

4 Claims, 2 Drawing Sheets

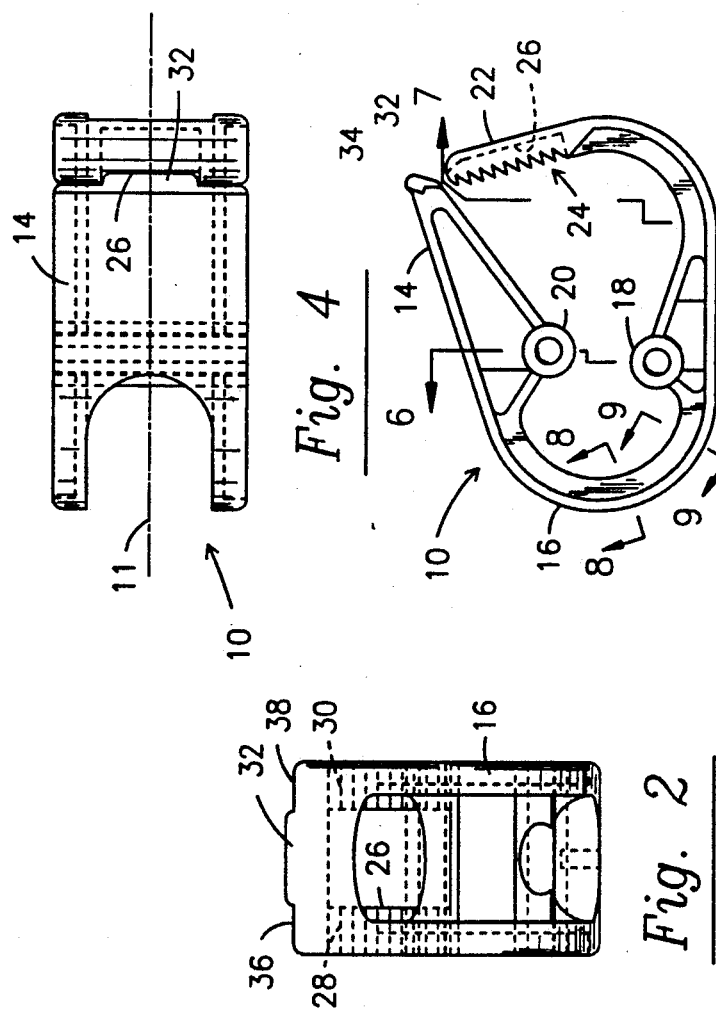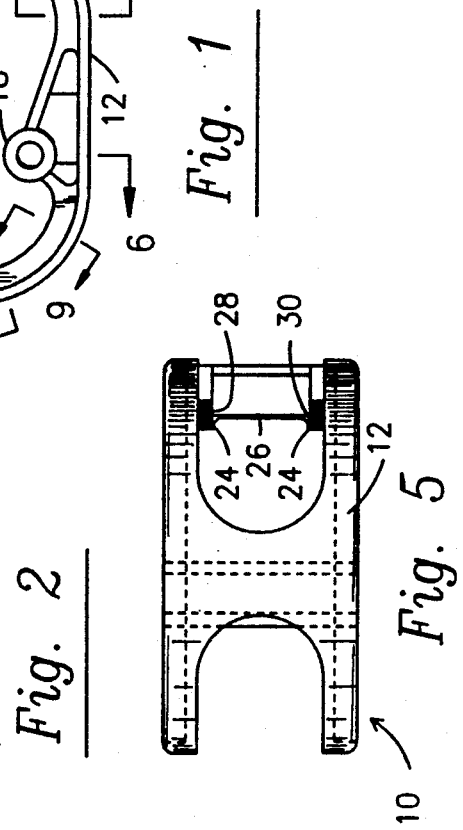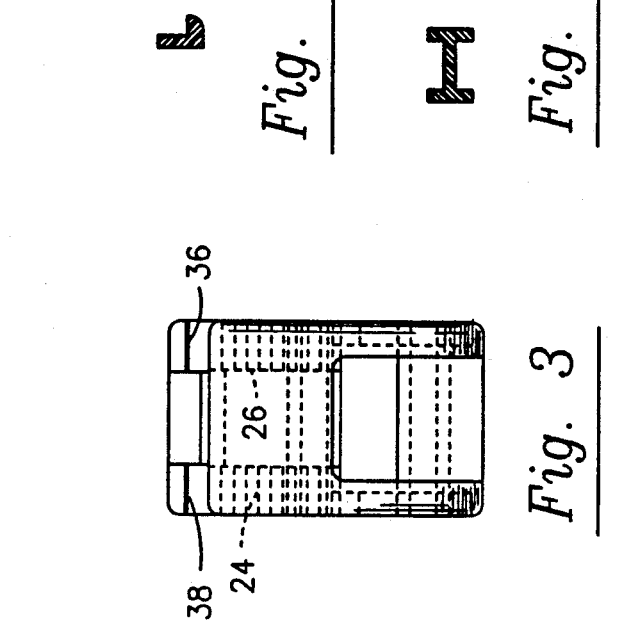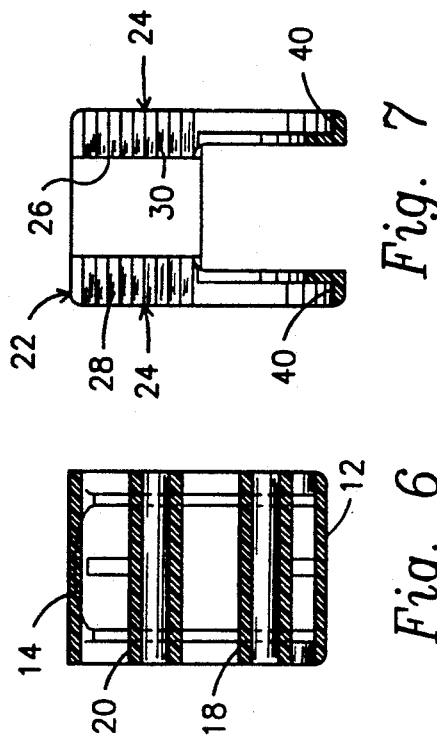

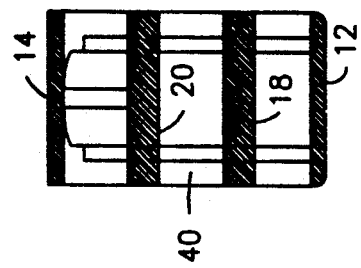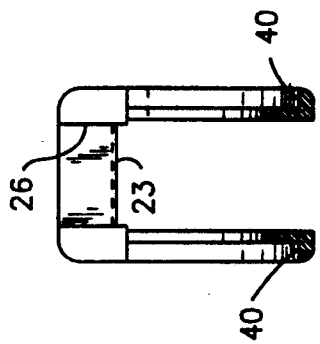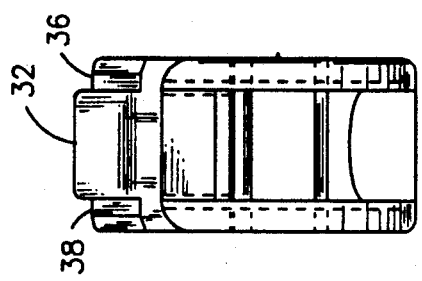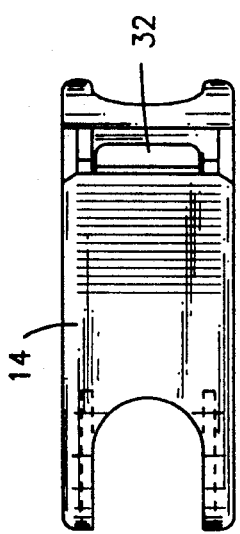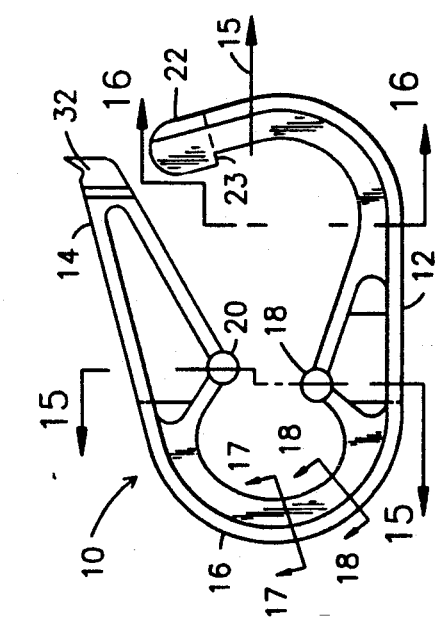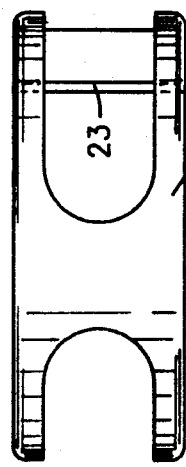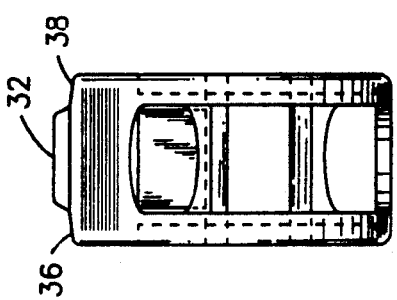

TUBE CLAMP

TECHNICAL FIELD

This invention relates, generally, to clamps of the type used to restrict or cut off the flow of liquid fluids flowing through a flexible tube or cannula.

BACKGROUND ART

The common tube clamp includes a flat base member or first leg and a flat closure member or second leg that extends in substantial parallelism to said base. The base and closure member are integrally formed with one another and are interconnected at their respective proximal ends by a flexible interconnecting means having the configuration of a return bend.

The first leg or base member terminates at its distal end in a substantially orthogonally disposed latch member having plural transversely disposed, equidistantly spaced teeth members formed on a proximal side thereof.

The second leg or closure member terminates in a leading edge that is adapted to selectively engage the interdental spaces of the toothed latch member and said leading edge is thus understood to function as a catch means.

Tube-pinching protuberance members are formed on the underside and topside, respectively, of the closure member and the base member, about mid-length thereof, in confronting relation to one another.

The clamp is carried by a tube that extends through an aperture formed in the return bend part of the clamp and that is positioned between the opposing protuberances. The tube is constricted to any desired degree by manually compressing the clamp at its leading end; the catch means at the leading free end of the closure member successively engages the teeth formed on the latch member until the desired amount of flow restriction is achieved and the desired position is maintained when the clamp is released by the interdental engagement of the catch and the teeth of the latch member. The clamp is released by lightly compressing the closure member to momentarily release the pressure between the latch and catch and displacing the flexible tooth-carrying latch member away from said catch to allow the closure member to resume its position of repose.

Earlier patents showing such tube clamps include U.S. Pat. Nos. 4,097,020 to Sussman and 3,942,228 to Buckman, et. al.

If carefully used, the tube clamps heretofore known are adequate to perform their intended function, especially if they are of metallic construction. Problems may arise, however, when the clamps are used carelessly. Health care professionals, e.g., are often required to handle very large workloads and must accomplish many tasks quickly. As a consequence, a nurse or doctor, intending to shut off an intravenous feed, may quickly squeeze the tube clamp very hard and walk away without visually inspecting the clamp to determine whether or not fluid flow has actually stopped. The common tube clamp, described above, is susceptible to skewing when closed with less than due care, especially if it is of plastic construction, as are most modern clamps. When skewing occurs, the tube is only partly pinched by the confronting protuberances and flow of liquid therethrough may continue. Skewing is caused by a failure to maintain the alignment of the catch and the latch, i.e., at the completion of a skewed closing, the longitudinal axis of the closure member is disposed at an angle relative to the longitudinal axis of the base member, and the protuberances formed integrally with said parts are misaligned with respect to one another and a full pinching action is not achieved.

An improved tube clamp is needed that would function properly even when closed in a careless manner, but the prior art, when considered as a whole, neither teaches nor suggests how the existing clamp could be improved.

DISCLOSURE OF INVENTION

The longstanding but heretofore unfulfilled need for a tube clamp that is not susceptible to skewing even when carelessly manipulated is now fulfilled by a novel tube clamp construction of tongue and groove design. In a first embodiment, a tongue projects distally of the distal free end of the closure member, and is slidably received within a complementally formed groove formed in the proximal face of the resilient latch member. The groove is flanked by teeth and the tongue is flanked by the catch means that engages said teeth. The groove thus constrains the tongue to slide therein, thereby maintaining the catch member in registration with the latch member, and maintaining the longitudinal axis of the closure member in alignment with the longitudinal axis of the base. The protuberances are thus maintained in alignment with one another, resulting in a completely shut off tube when the clamp has been squeezed.

The primary object of this invention is to provide a skew-free tube clamp.

Additional objects, features and advantages of this invention will become apparent as this description proceeds.

The invention accordingly comprises the features of construction, combination of elements and arrangement of parts that will be exemplified in the construction set forth hereinafter and the scope of the invention will be set forth in the claims.

DESCRIPTION OF THE DRAWINGS

For a fuller understanding of the nature and objects of the invention, reference should be made to the following detailed description, taken in connection with the accompanying drawings, in which:

FIG. 1 is a side elevational view of a first embodiment of the present invention;

FIG. 2 is a rear end elevational view thereof;

FIG. 3 is a front end elevational view thereof;

FIG. 4 is a top plan view thereof;

FIG. 5 is a bottom plan view thereof;

FIG. 6 is a sectional view taken along line 6—6 in FIG. 1;

FIG. 7 is a sectional view taken along line 7—7 in FIG. 1;

FIG. 8 is a sectional view taken along line 8—8 in FIG. 1;

FIG. 9 is a sectional view taken along line 9—9 in FIG. 1;

FIG. 10 is a side elevational view of a second embodiment of the present invention;

FIG. 11 is a rear end elevational view thereof;

FIG. 12 is a front end elevational view thereof;

FIG. 13 is a top plan view thereof;

FIG. 14 is a bottom plan view thereof;

FIG. 15 is a sectional view taken along line 15—15 in FIG. 1;

FIG. 16 is a sectional view taken along line 16—16 in FIG. 1;

FIG. 17 is a sectional view taken along line 17—17 in FIG. 10; and

FIG. 18 is a sectional view taken along line 18—18 in FIG. 10.

Similar reference numerals refer to similar parts throughout the several views of the drawings.

BEST MODES FOR CARRYING OUT THE INVENTION

Referring now to FIG. 1, it will there be seen that an exemplary embodiment of the invention is denoted by the reference numeral 10 as a whole.

Clamp 10 includes a generally flat, longitudinally extending base means or first leg member 12, a generally flat, longitudinally extending closure means or second leg member 14, and a flexible and resilient interconnecting means 16 in the form of a return bend that interconnects said base and closure means at their respective proximal ends.

A transversely disposed rigid protuberance 18, formed integrally with base member 12, is disposed in confronting relation to similar protuberance 20 formed integrally with closure member 14.

A latch means 22 is provided at the distal end of base member 12, in substantially orthogonal relation thereto and in integral formation therewith; a plurality of transversely disposed teeth members 24 are formed on a proximal side thereof.

Groove 26 bisects said teeth as perhaps best shown in FIGS. 5 and 7; accordingly, latch means 22 is collectively formed in part by said transversely spaced apart first and second teeth members 28, 30.

The leading end of closure member 14 has a distally projecting tongue member 32; thus, catch means 34 is collectively formed by first and second edges or parts 36, 38 that flank said tongue member (FIG. 2) When said edges 36, 38 interdentally engage their associated teeth 28, 30, the sliding interlocking of tongue 32 and groove or channel 26 constrains the catch and latch means to be in complete registration with one another, i.e., the longitudinal axis of symmetry 11 (FIG. 4) of base 12 will remain in unskewed alignment with the longitudinal axis of closure member 14. This insures that confronting protuberances 18, 20 will fully close the cannula to fluid flow whenever the clamp is closed.

In a second embodiment, shown in FIGS. 8–14, latch 22 is not provided with teeth as in the first embodiment but it is still bisected by groove 26 (FIG. 14). Tongue 32 is received by said groove and leading edges 36, 38 engage and catch lower lip 23 of said latch member 22. To open clamp 10, flexible and resilient latch 22 is pressed with a thumb in the direction indicated by arrow 15 in FIG. 8; there is no need to first compress parts 12 and 14 toward one another. The other parts of this second embodiment are substantially in common with the corresponding parts of the first embodiment.

In both embodiments, the outer edges of the clamps may have an angle iron construction as shown in FIG. 7 as at 40 and as best shown in FIGS. 8 and 17, respectively. An I-beam configuration is also within the scope of this invention as shown in FIGS. 9 and 18. Such construction strengthens the clamp while allowing it to be made of less materials. The cross sectional views of FIGS. 8, 9, 17, and 18 should of course be understood as depicting alternate embodiments, i.e., interconnecting means 16 is either of angled construction or I-beam construction and both constructions would not exist in the same piece, of course, as might be inferred from the placing of the FIG. lines on FIGS. 1 and 10.

This invention is clearly new and useful. Moreover, it was not obvious to those of ordinary skill in this art at the time it was made, in view of the prior art, taken as a whole.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. In a tube clamp, comprising:

an elongate base member having a longitudinal axis of symmetry;

an elongate closure member having a longitudinal axis of symmetry that is disposed in parallelism with said base member longitudinal axis of symmetry;

a flexible interconnecting means in the form of a return bend for interconnecting respective proximal ends of said base and closure members;

a latch member formed integrally with a distal end of said base member and being disposed substantially in orthogonal relation thereto;

a catch means formed in a distal end of said closure member;

a plurality of transversely disposed teeth members being formed in said latch member;

a groove member formed in said latch member;

said groove member having a width equal to about one-half the width of said latch member;

said groove member being centered with respect to said latch member;

teeth members on opposite side of said groove member having a common transverse extent equal to about one-quarter the transverse extent of said latch member;

a tongue member formed in said catch means, said tongue member projecting distally relative to said catch means;

said tongue member having a width slightly less than the width of said groove member, said tongue member therefor having a width equal to about one-half the width of said catch means;

said tongue member being centered with respect to said catch means;

catch means on opposite sides of said tongue having a common transverse extent equal to about one-quarter the transverse extent of said catch means;

said tongue member being slidably received within said groove member; and said catch means being selectively engageable with said teeth members on opposite sides of said tongue and groove members;

whereby the respective longitudinal axes of symmetry of said base and closure members are maintained in parallelism with one another when the respective distal ends of said base and closure members are driven toward one another.

2. In the clamp of claim 1, further comprising:

a first protuberance formed base member substantially mid-length thereof in projecting relation toward said closure member;

a second protuberance formed integrally with said closure member substantially mid-length thereof in projecting relation toward said base member;

said first and second protuberances being disposed in confronting relation to one another;

an aperture being formed in said interconnecting means so that a flexible tube may extend therethrough, said tube further extending between said first and second protuberances so that it is at least partially constricted by said first and second protuberances when said clamp is at least partially closed.

3. A tube clamp, comprising:

a pair of generally parallel, transversely spaced apart leg members;

a return bend means interconnecting said leg members to one another at a first end thereof;

said return bend means having a cross section of predetermined configuration;

an aperture formed in said return bend;

a first protuberance formed substantially mid-length of a first leg member;

a second protuberance formed substantially mid-length of a second leg member;

said first and second protuberances being disposed in confronting, cooperative relation to one another;

a latch member formed integrally with said first leg member in substantially orthogonal relation thereto;

a plurality of equidistantly spaced, transversely disposed tooth members formed in a proximal side of said latch member;

a groove member formed in said proximal side of said latch member;

said groove member having a predetermined depth;

said groove member bisecting said tooth members into first and second parts;

said groove member having a width equal to about half the width of said latch member;

tooth members on opposite sides of said groove member having a common transverse extent equal to about one-quarter the transverse extent of said latch member;

a catch means formed at a distal free end of said second leg member;

a tongue member formed integrally with said distal free end and projecting distally therefrom by a distance slightly less than the predetermined depth of said groove member;

said tongue member bisecting said catch means into first and second parts;

said tongue member having a width slightly less than the width of said groove member, said tongue member therefor having a width equal to about one-half the width of said catch means;

said tongue member being centered with respect to said catch means;

said first and second parts of said catch means being on opposite sides f said tongue and having a common transverse extent equal to about one-quarter the transverse extent of said catch means;

said tongue member being slidably received within said groove member;

said first and second parts of said catch means being disposed in full interdental registration with said first and second parts of said tooth members, respectively, when said tongue member is so disposed;

whereby said first and second protuberances are in full registration with one another when said clamp is closed so that no fluid may flow through said tube.

4. A tube clamp, comprising:

a first leg member and a second leg member having a common longitudinal axis of symmetry;

a flexible return bend means formed integrally with said first and second leg members;

said flexible return bend means having a cross section of predetermined configuration;

a tube-receiving aperture being formed in said return bend;

a pair of cooperatively positioned protuberance members being formed on opposite leg members, said protuberance members being operative to constrict a tube received by said aperture;

a latch member disposed substantially orthogonally to said first leg member and being integrally formed therewith;

a transverse lip member being formed in a preselected surface of said latch member;

a groove formed in said lip member;

said groove having a width equal to about half the width of said latch member;

said groove being centered with respect to said latch member;

said groove dividing said lip member into first and second lip members;

said first and second lip members being on opposite sides of said groove and having a common transverse extent equal to about one-quarter the transverse extent of said latch member;

a tongue member, complementally formed in relation to said groove member, said tongue member being formed at a free end of said second leg member;

a pair of catch members disposed in flanking relation to said tongue member;

said tongue member having a width slightly less than the width of said groove member, said tongue member therefor having a width equal to abut one-half the width of said second leg member;

said tongue member being centered with respect to said second leg member and dividing said second leg member into first and second catch means;

said first and second catch means being on opposite sides of said tongue and having a common transverse extent equal to about one-quarter the transverse extent of said second leg member;

said first and second catch means engaging opposite ends of said lip member when said first and second leg members are driven toward one another;

whereby said tube is substantially unconstricted when said first and second catch means are not in engagement with their associated opposite ends of said lip member;

whereby said tube is substantially completely constricted when said first and second catch means are engaged to said opposite ends of said lip member; and whereby said tongue and groove members maintain said first and second leg members and hence said protuberance members in alignment with one another even if said leg members are carelessly driven toward one another.

* * * * *